(12) United States Patent
Gately et al.

(10) Patent No.: US 6,531,619 B1
(45) Date of Patent: Mar. 11, 2003

(54) PREPARATION OF CYCLOPENTADIENYL OR INDENYL TITANIUM TRIHALIDES

(75) Inventors: Daniel A. Gately, Berthoud, CO (US); Jeffrey M. Sullivan, Loveland, CO (US); Karin A. Voll Barclay, Boulder, CO (US); Dawn A. Arkin, Longmont, CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 10/042,002

(22) Filed: Jan. 8, 2002

(51) Int. Cl.[7] .............. C07F 17/00; C07F 7/28; B01J 31/00
(52) U.S. Cl. .............. 556/52; 502/152; 526/160; 526/943
(58) Field of Search .............. 556/52; 502/152; 526/160, 943

(56) References Cited

U.S. PATENT DOCUMENTS

| | | | | |
|---|---|---|---|---|
| 2,917,501 A | * | 12/1959 | Drucker et al. | 526/137 |
| 3,046,288 A | * | 7/1962 | Sloan et al. | 556/52 |
| 3,072,691 A | * | 1/1963 | Gorsich | 556/52 |
| 3,080,305 A | * | 3/1963 | Gorsich | 204/157.75 |
| 3,161,629 A | * | 12/1964 | Gorsich | 556/52 |
| 5,721,327 A | * | 2/1998 | Santi et al. | 526/133 |
| 5,858,904 A | * | 1/1999 | Takeuchi et al. | 502/124 |

* cited by examiner

Primary Examiner—Porfirio Nazario-Gonzalez
(74) Attorney, Agent, or Firm—Edward S. Irons

(57) ABSTRACT

Cyclopentadienyl or indenyl titanium trichlorides are produced by converting a cyclopentadiene or an indene to a corresponding cyclopentadienyl or indenyl titanium trialkoxide which is treated with a halogenating agent to provide the desired cyclopentadienyl or indenyl titanium trichloride.

4 Claims, No Drawings

PREPARATION OF CYCLOPENTADIENYL OR INDENYL TITANIUM TRIHALIDES

FIELD OF THE INVENTION

This invention relates to the preparation of cyclopentadienyl or indenyl titanium trihalides.

BACKGROUND OF THE INVENTION

Known methods for the synthesis, of cyclopentadienyl titanium trichlorides may require the use of titanium(III) trichloride, involve reduction-oxidation procedures, or the use of solvents, e.g., tetrahydrofuran (THF) or glyme, which are difficult to remove.

One such known synthesis entails treatment of pentamethyl cyclopentadiene with potassium tertiary butoxide to provide potassium pentamethyl cyclopentadiene which must then be treated with trimethyl silicon chloride (TMSCl) to obtain the desired pentamethyl cyclopentadienyl trichloride. The synthesis of the potassium pentamethyl cyclopentadiene results in a reaction mixture that contains tertiary butyl alcohol which is difficult to remove.

There is a need for an improved, cost effective synthesis of cyclopentadienyl and indenyl trichlorides which avoids these disadvantages.

SUMMARY OF THE INVENTION

A cyclopentadiene or indene is lithiated in THF or ethyl ether and treated with $XTi(OiPr)_3$ wherein X is a halogen to produce a THF or ether solution of cyclopentadienyl or indenyl titanium tri-isopropoxide and a lithium halide. The THF or ethereal solvent is exchanged for a hydrocarbon solvent to precipitate the lithiumihalide which is separated by filtration. The mother liquor which contains cyclopentadienyl or indenyl titanium tri-isopropoxide is treated with $SiCl_4$ or $BCl_3$ to provide cyclopentadienyl or indenyl titanium trihalide.

DESCRIPTION OF THE INVENTION

In this specification, the expressions "cyclopentadiene" and "indene" mean cyclopentadiene or indene per se or any alkyl cyclopentadiene or alkyl indene which has one or more, preferably $C_1$ to $C_6$ alkyl ring substituents. The ring substituents may be the same or different.

Pursuant to one embodiment of the invention, a cyclopentadiene or an indene is deprotonated with butyllithium in THF or similar solvent in which the lithiated cyclopentadiene or indene and the lithium chloride are each soluble. Useful solvents other than THF include diethyl ether and monoglyme. $ClTi(OiPr)_3$, in which the expression "(OiPr)" means isopropoxide, is added to the deprotonated reaction mixture which is then heated, preferably at reflux, for 6 to 8 hours to provide a second reaction mixture that contains a cyclopentadienyl or indenyl titanium tri-isopropoxide and lithium chloride.

The reaction mixture solvent is exchanged for an aliphatic hydrocarbon solvent, e.g., Isopar®E, to precipitate the LiCl which is removed by filtration.

The filtrate, a solution of a cyclopentadienyl or indenyl titanium tri-isopropoxide, is treated with $SiCl_4$, $AlCl_3$ or $BCl_3$, preferably at reflux in an amount at least stoichiometrically appropriate, to provide the corresponding cyclopentadiene titanium trichloride.

Any compound of the formula $XTi(OR)_3$, in which X is a halogen, preferably chlorine, and R is an alkyl group, preferably a $C_1$ to $C_6$ alkyl group, may be used instead of $ClTi(OiPr)_3$.

EXAMPLE 1

Pentamethylcyclopentadiene is deprotonated with butyllithium in THF. See Equation 1:

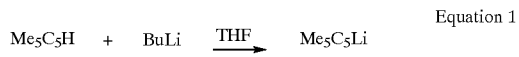

Equation 1

The lithenide is treated in situ with $ClTi(OiPr)_3$ at reflux for 6 to 8 hours. THF was distilled until the residual amount was less than 1% by GMCS. Isopar®E, an aliphatic hydrocarbon, was added to precipitate LiCl. The intermediate pentamethylcyclopentadiene titanium tri-isopropoxide in solution in Isopar®E was filtered away-from the LiCl. The cake was washed with hexanes. See Equation 2:

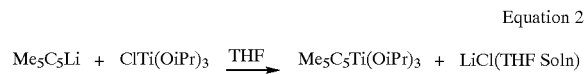

Equation 2

The THF solvent was exchanged for Isopar® E to precipitate LiCl. The LiCl was separated by filtration. The filtrate was treated with 2.2 eq $SiCl_4$ and refluxed to provide $Me_5C_5TiCl3$. The reaction mixture was cooled to room temperature. The product was removed by filtration to provide a pentamethylcyclopentadienyl titanium trichloride cake. Yield=70–80% based on pentamethylcyclopentadiene.

EXAMPLE 2

Preparation of 2-Methyl Indene Titanium Trichloride 2-methyl indene was deprotonated by treatment with butyllithium in hexanes.

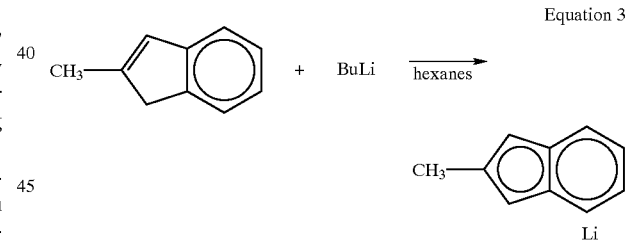

Equation 3

In a separate vessel, $TiCl_4$ was added to 3 equivalents of neat $Ti(OiPr)_4$ to produce $Ti(OiPr)_3$:

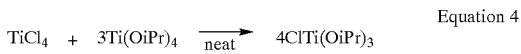

Equation 4

The deprotonated 2-methyl indene was treated with $ClTi(OiPr)_3$ and stirred out for three hours at room temperature. The reaction mixture contained tris isopropoxy titanium 2-methyl indene which was separated by filtration:

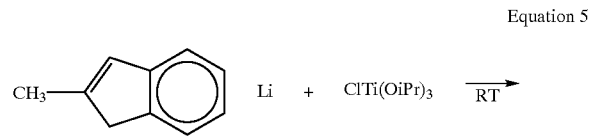

Equation 5

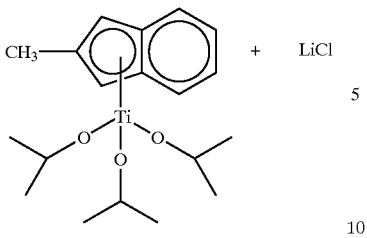

+ LiCl

The tris isopropoxy titanium 2-methyl indene was treated with 1.5 equivalents of $BCl_3$ or 1.2 equivalents of solid $AlCl_3$:

Equation 6

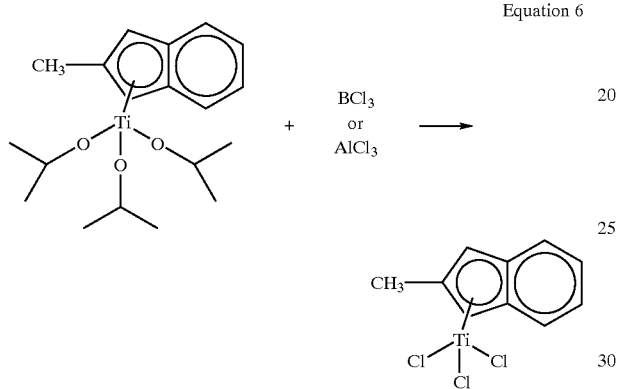

The solvent exchange and the work up were like that described in Example 1.

Either halogenation reagent provides 80% to 90% yields of the desired 2-methyl indenyl titanium trichloride.

We claim:

1. A method for the preparation of a cyclopentadienyl or indenyl titanium trihalide which comprises:
   (i) treating a lithiated cyclypentadiene or indene compound with a compound of the formula $XTi(OR)_3$
      wherein X is a halogen,
      wherein R is alkyl, and
      wherein a cyclopentadienyl or indenyl titanium trialkoxide is produced; and
   (ii) treating said trialkoxide with $SiCl_4$ or $BCl_3$,
      wherein a cyclopentadienyl or indenyl titanium trihalide is produced.

2. A method which comprises:
   (i) treating a lithiated pentamethylcyclopentadiene with $ClTi(OiPr)_3$ in THF or ethyl ether.
      wherein a first reaction mixture containing the compound

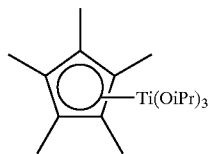

and LiCl in solution in THF or ethyl ether is produced;
   (ii) exchanging said THF or ether in said first reaction mixture with a hydrocarbon medium in which said LiCl is insoluble
   (iii) removing said LiCl to provide a LiCl-free hydrocarbon solution of the compound which is the product of step (i); and
   (iv) treating said LiCl-free step (iii) hydrocarbon solution of the, compound which is the product of step (i) with silicon tetrachloride or boron trichloride,
      wherein a second reaction mixture comprising said hydrocarbon medium and particulate pentamethylcyclo-pentadienyl titanium trichloride is produced.

3. The method of claim 2 further comprising the additional step
   (v) separating said particulate pentamethylcyclo-pentadienyl trichloride from said second reaction mixture.

4. A method which comprises:
   (i) treating lithiated indene having at least one alkyl ring substituent with $ClTi(OiPr)_3$ in THF or ethyl ether, wherein a first reaction mixture containing

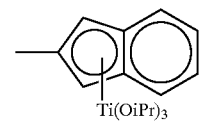

and LiCl in solution in THF or ethyl ether is produced;
   (ii) exchanging said THF or ether in said first reaction mixture with a hydrocarbon medium in which said LiCl is insoluble;
   (iii) removing said LiCl to provide a LiCl-free hydrocarbon solution of the product of step (i); and
   (iv) treating said LiCl-free step (iii) hydrocarbon solution of the product of step (i) with silicon tetrachloride, $BCl_3$ or $AlCl_3$,
      wherein a second LiCl-free reaction mixture comprising said hydrocarbon medium and particulate. pentamethylcyclo-indene titanium trichloride is produced, and
      wherein said indene has at least one alkyl ring substituent.

* * * * *